United States Patent [19]

Magarian et al.

[11] 4,442,119
[45] Apr. 10, 1984

[54] CYCLOPROPYL ANALOGS AS ESTROGENIC AS ANTI-FERTILITY AGENTS

[75] Inventors: Robert A. Magarian; Joseph T. Pento, both of Norman, Okla.

[73] Assignee: The Board of Regents for the University of Oklahoma, Norman, Okla.

[21] Appl. No.: 402,112

[22] Filed: Jul. 26, 1982

Related U.S. Application Data

[63] Continuation-in-part of Ser. No. 166,081, Jul. 7, 1980, abandoned.

[51] Int. Cl.$^3$ .................... A01N 43/36; A61K 31/40; A01N 29/04
[52] U.S. Cl. .................................. 424/274; 424/346; 424/353
[58] Field of Search .................. 424/274, 346, 353

[56] References Cited

PUBLICATIONS

Magarian et al., "2-Chloro-1-phenylindene from 1,1-Dichloro-trans-2,3-diphenylcyclopropane", Jour. Pharm. Sciences, (1972), vol. 61, pp. 1216–1219.

Magarian et al., "Synthesis of Cyclopropyl Analogs of Stilbene and Stilbenediol as Possible Antiestrogens", Jour. Pharm. Sciences, (1975), vol. 64, No. 10, pp. 1626–1632.

Hausser et al., "Solvolysis of Cyclopropyl Halides, III, 2,3-Diphenylcyclopropyl Chlorides", J. Org. Chem., 37:4087–4090 (1972).

Primary Examiner—Elbert L. Roberts
Attorney, Agent, or Firm—Dunlap & Codding

[57] ABSTRACT

Estrogenic cyclopropyl analogs, when administered to a female subject, function as anti-fertility agents to prevent pregnancy in the subject. Further, the estrogenic cyclopropyl analogs may be used as estrogenic agents to produce an estrogenic response in a female subject. The estrogenic cyclopropyl analogs useful as estrogenic agents have the general structure:

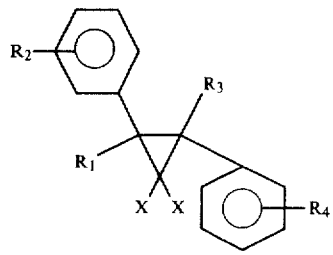

wherein:
  X is a halogen or hydrogen atom;
  $R_1$ is a hydrogen atom, an alkyl group containing from 1 to about 3 carbon atoms, a monocyclic group, a hydroxy substituted monocyclic group, or an alkoxy substituted monocyclic group in which the alkyl substitutent contains from 1 to about 3 carbon atoms;
  $R_2$ is a hydrogen atom, an acetate group, a hydroxyl group, an alkoxy group in which the alkyl substituent contains from 1 to about 3 carbon atoms, a beta-dialkylaminoethoxy group in which the alkyl substituent contains from 1 to about 3 carbon atoms, a beta-monoaminoheterocycloethoxy group, or pharmaceutically acceptable salts thereof;
  $R_3$ is a hydrogen atom, or an alkyl group containing from 1 to about 3 carbon atoms;
  $R_4$ is a hydrogen atom, an acetate group, a hydroxyl group, or an alkoxy group in which the alkyl substituent contains from 1 to about 3 carbon atoms.

19 Claims, No Drawings

CYCLOPROPYL ANALOGS AS ESTROGENIC AND ANTI-FERTILITY AGENTS

CROSS-REFERENCE TO RELATED APPLICATION

This application is a continuation in part of U.S. patent application Ser. No. 166,081, filed July 7, 1980 now abandoned.

FIELD OF THE INVENTION

This invention relates to estrogenic agents and their use as estrogens, and more particularly, but not by way of limitation, to the use of estrogenic cyclopropyl analogs as female anti-fertility agents.

DESCRIPTION OF THE PRIOR ART

Cyclopropyl analogs, such as 1,1-dichloro trans-2,3-diphenylcyclopropane, have heretofore been known. Such cyclopropyl analogs have been prepared using two different synthetic methods, namely, a two-phase catalytic method and an organomercurial method. Such gem-dichlorocyclopropyl analogs have also been reduced to their corresponding cyclopropyl analog via sodium and wet methanol.

Natural and synthetic estrogens have heretofore been employed in a number of therapeutic applications. For example, estrogens have been employed to prevent spontaneous abortions during pregnancy, for treatment of estrogen deficiency effects of menopause, skin softeners and the like. However, the existing estrogens are known to produce a variety of side-effects and toxicities; such as, thromboemboli, hypertension, fluid retention, headaches, hyperglycemia, mental depression, etc., which often limit or complicate their therapeutic use.

SUMMARY OF THE INVENTION

According to the present invention we have discovered that estrogenic cyclopropyl analogs can be used as an estrogenic or anti-fertility agents in a subject. The estrogenic cyclopropyl analogs which can be administered in non-toxic dosages to subjects are represented by the general structure

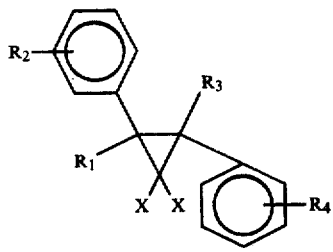

wherein:

X is a halogen or hydrogen atom;

$R_1$ is a hydrogen atom, an alkyl group containing from 1 to about 3 carbon atoms, a monocyclic group, a hydroxy substituted monocyclic group, or an alkoxy substituted monocyclic group in which the alkyl substituent contains from 1 to about 3 carbon atoms;

$R_2$ is a hydrogen atom, an acetate group, a hydroxyl group, an alkoxy group in which the alkyl substitutuent contains from 1 to about 3 carbon atoms, a beta-dialkylaminoethoxy group in which the alkyl substituent contains from 1 to about 3 carbon atoms, a beta-monoaminoheterocycloethoxy group; or pharmaceutically acceptable salts thereof;

$R_3$ is a hydrogen atom, or an alkyl group containing from 1 to about 3 carbon atoms; and $R_4$ is a hydrogen atom, an acetate group, a hydroxyl group, or an alkoxy group in which the alkyl substituent contains from 1 to about 3 carbon atoms.

The estrogenic cyclopropyl analogs defined above have been found to specifically bind to the uterine estrogen receptor, although less intensely than the presently available natural and synthetic estrogen compounds.

Therefore, an object of the present invention is to provide an improved anti-fertility agent which can readily be administered to a subject and reduce or inhibit ovulation, implantation, and pregnancy.

Another object of the present invention is to provide improved anti-fertility agents which do not possess serious side-effects found in current female anti-fertility agents.

Another object is to provide improved estrogenic agents which do not possess serious, harmful side effects in the subject when same is administered as an estrogenic agent.

These and other objects, advantages and features of the present invention will be apparent to those skilled in the art from a reading of the following detailed description when read in conjunction with the drawings which accompany this disclosure and with the appended claims.

DETAILED DESCRIPTION OF PREFERRED EMBODIMENTS

As previously stated, the present invention relates to estrogenic cyclopropyl analogs and their use as anti-fertility agents in the prevention of ovulation, implantation and pregnancy. In addition, such cyclopropyl analogs may find additional use as general estrogenic agents and in estrogen replacement therapy in the female subject.

In order to assist in the understanding of the subject invention, as well as the terminology used herein, the following definitions are set forth.

The term "estrogen" is to be understood to be a substance which stimulates the growth, maturation, and development of estrogen target tissues (e.g., breasts, ovaries, uterine tissue, etc.) which physiologic responses are designated as estrogenic responses or as estrogenic activity.

"Dosage" is the amount of the cyclopropyl analog administered to a subject during a twenty-four (24) hour period to produce the desired therapeutic effect within the subject.

The term "subject" as used herein is to be understood to include humans, household animals, such as dogs and cats, laboratory animals, such as rats and mice, and large animals such as horses, cattle and the like.

As previously stated, we have discovered that estrogenic cyclopropyl analogs, when employed as anti-fertility agents, substantially prevent or retard the implantation and pregnancy in a subject. The estrogenic cyclopropyl analogs which can be administered to a subject as an anti-fertility agent in accordance with the present invention are generally represented by the structure:

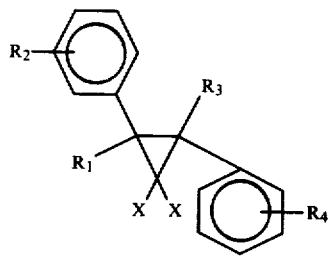

wherein:

X is a halogen or hydrogen atom;

$R_1$ is a hydrogen atom, an alkyl group containing from 1 to about 3 carbon atoms, a monocyclic group, a hydroxy substituted monocyclic group, or an alkoxy substituted monocyclic group in which the alkyl substituent contains from 1 to about 3 carbon atoms.

$R_2$ is a hydrogen atom, an acetate group, a hydroxyl group, an alkoxy group wherein the alkyl substituent contains from 1 to about 3 carbon atoms, a beta-dialkylaminoethoxy group in which the alkyl substituent contains from 1 to about 3 carbon atoms, a beta-monoaminoheterocycloethoxy group, or pharmaceutically acceptable salts thereof;

$R_3$ is a hydrogen atom, or an alkyl group containing from 1 to about 3 carbon atoms; and $R_4$ is a hydrogen atom, an acetate group, a hydroxyl group, or an alkoxy group in which the alkyl substituent contains from 1 to about 3 carbon atoms.

Any suitable estrogenic cyclopropyl analog meeting the above definition can be employed as the anti-fertility agent, to prevent ovulation, implantation and pregnancy in the subject. Illustrative of estrogenic cyclopropyl analogs satisfying the above-defined structure and which can be employed as anti-fertility agents, in accordance with the present invention are as follows:

1,1-dichloro-trans-2,3-diphenylcyclopropane
1,1-dichloro-trans-2,3-diethyl-2,3-(4,4'-dimethoxyphenyl)cyclopropane
1,1-dichloro-trans-2,3-diethyl-2,3-(4,4'-diacetoxyphenyl)cyclopropane
1,1-dichloro-trans-2,3-diethyl-2,3-(4,4'-dihydroxyphenyl)cyclopropane
1,1-dichloro-trans-2,3-(4,4'-dimethoxyphenyl)cyclopropane
trans-1,2-Diphenylcyclopropane
1,2-diethyl-trans-1,2-(4,4'-dimethoxyphenyl)cyclopropane
1,2-diethyl-trans-1,2-(4,4'-dihydroxyphenyl)cyclopropane
trans-1,2-Bis-(p-methoxyphenyl)cyclopropane
trans-1,2-dimethyl-1,2-(4,4'-dimethoxyphenyl)cyclopropane
trans-1,2-dimethyl-1,2-diphenylcyclopropane
1-methyl-trans-1,2-(4,4'-dimethoxyphenyl)cyclopropane
trans-1-methyl-1,2-diphenylcyclopropane
1,1-dichloro-trans-2,3-diethyl-2,3-diphenylcyclopropane
1,1-dibromo-trans-2,3-diethyl-2,3-diphenylcyclopropane
1,1-difluoro-trans-2,3-diethyl-2,3-diphenylcyclopropane
1,1-dichloro-(E)-2-{p-[2-(N,N-dimethylamino)ethoxy]phenyl}-3-cyclopropane
1,1-dichloro-(E)-2,3-Bis-{p-[2-(N,N-dimethylamino)ethoxy]phenyl}cyclopropane
1,1-dichloro-(E)-2-{p-[2-(N,N-diethylamino)ethoxy]phenyl}-3-phenylcyclopropane
1,1-dichloro-(E)-2,3-bis-{p-[2-(N,N-diethylamino)ethoxy]phenyl}cyclopropane
1,1-dichloro-(E)-2-[p-(2-N-pyrrolidinoethoxy)-phenyl]-3-phenylcyclopropane
1,1-dichloro-(E)-2,3-Bis-[p-(2-N-pyrrolidinoethoxy)-phenyl]cyclopropane
1,1-dichloro-trans-2-(p-hydroxyphenyl)-2,3-diphenylcyclopropane
1,1-difluoro-trans-2-(p-hydroxyphenyl)-2,3-diphenylcyclopropane
1,1-dibromo-trans-2-(p-hydroxyphenyl)-2,3-diphenylcyclopropane Reduced Analogs (E)-1-{p-[N,N-dimethylamino)ethoxy]-phenyl}2-phenylcyclopropane
(E)-1,2-Bis-{p-[2-(N,N-dimethylamino)ethoxy]phenyl}cyclopropane
(E)-1-{p-[2-(N,N-dimethylamino)ethoxy]-phenyl}-2-phenylcyclopropane
(E)-1,2-Bis-{p-[2-(N,N-dimethylamino)ethoxy]phenyl}cyclopropane
(E)-1-[p-(2-N-pyrrolidinoethoxy)phenyl]-2-phenylcyclopropane
(E)-1,2-Bis-[p-(2-N-pyrrolidinoethoxy)phenyl]cyclopropane Pharmaceutically Acceptable Salts of Cyclopropyl Analogs 1,1-dichloro-(E)-2-{p-[2-(N,N-dimethylamino)ethoxy]phenyl}-3-phenylcyclopropane hydrochloride
(E)-1-{p-[2-N,N-dimethylamino)ethoxyphenyl}-2-phenylcyclopropane methanesulfonate
1,1-dichloro-(E)-2-{p-[2-(N,N-dimethylamino)ethoxy]phenyl}-3-phenylcyclopropane methanesulfonate
(E)-1-{p-[2-(N,N-dimethylamino)ethoxy]phenyl}-2-phenylcyclopropane methanesulfonate
1,1-dichloro-(E)-2-[p-(2-N-pyrrolidinoethoxy)phenyl]-3-phenylcyclopropane methanesulfonate
(E)-1-[p-(2-N-pyrrolidinoethoxy)phenyl]-2-phenylcyclopropane hydrochloride
(E)-1,2-Bis-{p-[2-(N,N-dimethylamino)ethoxy]phenyl{-cyclopropane dihydrochloride
(E)-1,2,Bis-{p-[2-(N,N-diethylamino)ethoxy]phenyl}-cyclopropane dihydrochloride
(E)-1,2-Bis-[p-(2-N-pyrrolidinoethoxy)phenyl]cyclopropane dihydrochloride
1,1-dichloro-(E)-2,3-Bis-{p-[2-(N,N-dimethylamino)ethoxy]phenyl}cyclopropane sulfate
1,1-dichloro-(E)-2,3-Bis-{p-[2-(N,N-dimethylamino)ethoxy]phenyl}cyclopropane dihydrochloride
1,1-dichloro-(E)-2,3-Bis-[p-(2-N-pyrrolidinoethoxy)phenyl]cyclopropane sulfate As previously set forth, the estrogenic cyclopropyl analogs useful as anti-fertility agents in a subject are the trans-isomers. Initial studies have indicated that trans-isomers of the cyclopropyl analogs are more estrogenic and more effective than the cis-isomers of such cyclopropyl analogs in the treatment of a subject to prevent or retard ovulation, implantation or pregnancy in the subject.

While any of the before-defined moieties X,R$_1$,R$_2$,R$_3$, and R$_4$, as well as the different combinations of such moieties, can be utilized as the estrogenic cyclopropyl analog for use as anti-fertility agents in accordance with the present invention, it is believed that the most desirable effects may be obtained when the respective moieties of the estrogenic cyclopropyl analogs are as follows:

X is a chlorine, fluorine or bromine atom;

R$_1$ is a hydrogen atom, a phenyl group, a p-hydroxyphenyl group, or a p-methoxyphenyl group;

R$_2$ is a hydrogen atom, a beta-dimethylaminoethoxy group, a beta-diethylaminoethoxy group, a beta-pyrrolidinoethoxy group, or pharmaceutically acceptable salts thereof;

R$_3$ is a hydrogen atom or an ethyl group; and

R$_4$ is a hydrogen atom, a hydroxyl group, or a methoxy group;

The dosage of the anti-fertility agents (i.e., the estrogenic cyclopropyl analogs defined hereinbefore by the generic structure required to substantially prevent or retard ovulation, implantation and pregnancy in a subject) can vary widely and will be dependent, to a large degree, upon the weight of the subject, and the estrogenic properties of the particular cyclopropyl analog employed. However, it is believed that desirable results can be obtained when the cyclopropyl analogs used as anti-fertility agents are administered to the subject in a dosage of from about 0.25 milligram to about 1 milligram per kilogram of weight of the subject, and an effective dosage of the estrogenic cyclopropyl analog anti-fertility agents will generally be about 0.5 milligram per kilogram of weight of the subject.

The estrogenic cyclopropyl analogs which may be employed as estrogenic agents to induce an estrogenic response in a female subject are generally solid materials. Thus it may be desirable to suspend, emulsify, solubilize, or disperse the estrogenic cyclopropyl analog in a suitable vehicle to facilitate the administration of the anti-fertility agent to the subject. In such instance, any suitable vehicle can be employed provided the vehicle is inert to the estrogenic cyclopropyl analog and to the subject. Such vehicles and the methods for suspending, emulsifying, solublizing, or dispersing the estrogenic cyclopropyl analogs in a suitable vehicle are well known in the art of pharmaceutical formulations and thus a further description of same is not believed necessary herein.

The method of administration of the anti-fertility agents of the present invention (i.e. the estrogenic cyclopropyl analogs) to the subject can be by any suitable means known in the art. For example, the anti-fertility agent can be administered to the subject orally, by implantation, or by the parenteral route of administration which may include intravenous, intramuscular and subcutaneous techniques. As previously indicated, we believed that any suitable estrogenic cyclopropyl analog fulfilling the definition set forth hereinbefore can be employed as an anti-fertility agent to prevent ovulation, implantation, and pregnancy.

The estrogenic cyclopropyl analogs as hereinbefore defined also exhibit properties which indicate that such estrogenic cyclopropyl analogs may be useful as general estrogenic agents. In employing such estrogenic cyclopropyl analogs as general estrogenic agents, the dosage of the estrogenic agent, required to induce the estrogenic response in the female subject may vary widely and be dependent, to a large degree upon the weight of the subject, the route of administration employed in the application of the estrogenic cyclopropyl analog, and the particular estrogenic cyclopropyl analog employed. However, it is believed that the dosage of the estrogenic cyclopropyl analog used as a general estrogenic agent to stimulate an estrogenic response in a female subject would be in an amount of from about 0.25 milligram to about 1 milligram per kilogram of weight of the subject, and an effective dosage of the estrogenic cyclopropyl analog estrogenic agent would generally be about 0.5 milligram per kilogram of weight of the subject.

The estrogenic cyclopropyl analogs which may be employed as estrogenic agents to induce an estrogenic response in a female subject are generally solid materials. Thus it may be desirable to suspend, emulsify, solubilize, or disperse the estrogenic cyclopropyl analog in a suitable vehicle to facilitate the administration of the estrogenic agent to the subject. In such instance, any suitable vehicle can be employed provided the vehicle is inert to the estrogenic cyclopropyl analog and to the subject. Such vehicles and the methods for suspending, emulsifying, solubilizing, or dispersing the estrogenic cyclopropyl analogs in the vehicle are well known in the art of pharmaceutical formulations and thus a further description of same is not believed necessary herein.

The method of administration of the estrogenic cyclopropyl analog for use as an estrogenic agent to induce an estrogenic response in a female subject may be by any suitable means known in the art. For example, the estrogenic cyclopropyl analog may be administered to the subject orally, by implantation, or by the parenteral route of administration which may include intravenous, intramuscular and subcutaneous techniques.

In order to determine the effectiveness of the estrogenic cyclopropyl analogs as an anti-fertility agent in humans an animal model was employed. The animal model is described in detail in the experimental procedures section presented in Example I.

The following examples are given to illustrate the effectiveness of the estrogenic cyclopropyl analogs in substantially preventing ovulation, implantation and pregnancy. The examples are for illustrative purposes only and are not to be construed as unduly limiting the scope of the invention as hereinafter recited in the claims. All parts and percentages in the examples, unless otherwise specified, are parts by weight and weight percentages.

EXAMPLE I

A series of cyclopropyl analogs were prepared using the several procedures. In each instance the gem-dichlorocyclopropyl analogs were prepared by either procedure A or B. The reduced analogs (i.e. the analogs without gem-dichlorocyclopropyl groups) were prepared using either the Procedure A or B in combination with Procedure C. It should be noted however that in those instances where it was desirous that the analog contain a hydroxyl moiety on the phenyl ring, such as in the para position, Procedure A was followed.

In each of the following Procedures A and B 1,1-dichloro-trans-2,3-diphenylcyclopropane was prepared as an illustrative example of the cyclopropyl analogs for use in the practice of the present invention. When the gem-dichlorocyclopanes so prepared were reduced to remove the chlorine atoms, such reductions were carried out using sodium metal in wet methanol. Procedure C is illustrative of the beforementioned reductive procedure in which trans-1,2-diphenylcyclopropane was prepared.

Procedure A

Preparation of gem-dichlorocyclopropyl analogs.

3.6 g (0.02 mole) of trans-stilbene was added to 10.0 g (0.002 mole) of phenyl(bromodichloromethyl)mercury in benzene. After the resulting solution was refluxed with stirring under dry nitrogen and maintained at 82°–88° C. in an oil bath for 1.5 hour with stirring, phenylmercuric bromide precipitated (7.2 g, 92%) and the reaction mixture turned yellow. The relative proton absorption in the NMR spectrum showed small quantities of the unchanged olefin.

The mixture then was refluxed with stirring for an additional hour. The NMR spectrum of this mixture indicated that the olefin had reacted. Benzene was removed on a flash evaporator, yielding 6.5 g of crude product which was dissolved in petroleum ether (bp 30°–60° C.) and filtered to remove a small amount of white precipitate, mp 175° C. dec. The crude product was purified through a 2×18 cm column of neutral alumina (activity I) using purified petroleum ether (bp 30°–60° C.). A light yellow oil was eluted, which solidified after standing in a refrigerator overnight. The solid had a melting point range of 38°–40° C. and weighed 4.5 g (86%).

An analytical sample was obtained by sublimation. the sublimator was kept at 45° C. (0.03 mm) in an oil bath while the inner cold finger was maintained at −5° C. by cold water pump. The white needles melted at 39°–40° C. NMR and infrared spectra verified the product of 1,1-dichloro-trans-2,3-diphenylcyclopropane.

Procedure B

Preparation of 1,1-diphenylcyclopropane.

16.0 g (0.09 mole) of trans-stilbene and 2.0 g (0.008 mole) of triethylbenzylammonium chloride were dissolved in 300 g of chloroform contained in a 1-liter three-necked flask fitted with a mechanical stirrer, condenser, and dropping funnel. The flask was cooled in an ice water bath, and 200 g of ice-cold 50% sodium hydroxide solution was added dropwise. The mixture was stirred at 10°–20° C. for 6 hours and then at room temperature for 2 days. The dark brown mixture was diluted with 100 ml of water and filtered. Two layers were separated, and the aqueous layer was washed with three 50 ml portions of methylene chloride.

All organic extracts were combined, washed with water, and dried over anhydrous magnesium sulfate. The drying agent was filtered, and the chloroform was evaporated under reduced pressure, yielding 28 g of a dark brown oil. Distillation of the crude oil at 140° C. (0.5 mm) gave 20 g (86%) of a light yellow liquid, which solidified after several days at 5° C., mp 38°–40° C. In subsequent reactions the distilled compound was passed through neutral alumina (activity I), using petroleum ether (bp 30°–60° C.) as the eluent to remove a small amount of the decomposed products.

Procedure C

Reduction of trans-dichlorocyclopropyl analogs to remove the chloro groups.

To a 250-ml three-necked flask, fitted with a dry ice-acetone condenser and a dropping funnel, were added 3.3 g (0.012 mole) of 1,1-dichloro-trans-2,3-diphenylcyclopropane and 40 ml of ether. This solution was stirred (magnetic stirrer) and cooled in an ice water bath. Sodium metal (5.5 g, 0.25 g-atom) was added in small pieces as 60 ml of methanol-water (100:3.3 ml) was added dropwise. The sodium reacted after 2 hours, and a white solid was observed. When all of the sodium had reacted, 20 ml of water was added and the aqueous layer was extracted with two 30 ml portions of ether.

The aqueous phase was neutralized slowly and carefully in an ice-salt bath with concentrated hydrochloric acid and extracted with two 20 ml portions of ether. The ether extracts were dried over anhydrous magnesium sulfate and filtered. The solvent was evaporated at reduced pressure, and the light yellow liquid was distilled and collected in three fractions at 0.01 mm.

Fraction 1 (bp 38°–52° C.) was kerosene (used for storing sodium), fraction 2 (bp 67° C.) was a mixture, and fraction 3 (bp 90°–92° C.) yielded 1.6 g (69%) of 1,2-diphenylcyclopropane. NMR and infrared spectra verified the production of trans-1,2-diphenylcyclopropane.

The cyclopropyl analogs so prepared and utilized in the following test procedures are tabulated as follows:

TABLE I

| Analog No. | CYCLOPROPYL ANALOGS Chemical Name |
|---|---|
| I | 1,1-Dichloro-trans-2,3-diphenylcyclopropane |
| II | 1,1-Dichloro-cis-2,3-diphenylcyclopropane |
| III | Trans-1,2-Diethyl-1,2-(4,4'-dimethoxyphenyl)cyclopropane |
| IV | 1,1-Dichloro-trans-2,3-diethyl-2,3-(4,4'-dihydroxyphenyl) cyclopropane |
| V | 1,1-Dichloro-trans-2,3-diethyl-2,3-(4,4'-diacetoxyphenyl)cyclopropane |
| VI | 1,1-Dichloro-trans-2,3-(4,4'-dimethoxyphenyl) cyclopropane |
| VII | 1,1-Dichloro-trans-2,3-diethyl-2,3-(4,4'-dimethoxyphenyl) cyclopropane |
| VIII | Trans-1,2-Diethyl-1,2-(4,4'-dihydroxyphenyl)-cyclopropane |
| IX | Cis-1,2-Diphenylcyclopropane |
| X | Trans-1,2-Diphenylcyclopropane |

Procedure D

Biological Methods—Uterotropic Assay for Estrogenic and Anti-estrogenic Activity The assay for estrogenic activity employed immature Swiss-Webster mice weighing 10–14 g (approximately 21 days old). The animals were randomly distributed into groups containing 5–6 mice each. Estradiol and the compounds were dissolved separately in sesame oil and administered subcutaneously in a volume of 0.1 ml. Control animals were treated with the same volume of sesame oil alone.

All animals were treated daily for three consecutive days. On the fourth day the animals were sacrificed and the uteri carefully dissected, blotted lightly and weighed to the nearest 0.1 mg. Body weights were also recorded. Estradiol was used in a dosage range of 0.01–0.04 ug (total dose) as the assay standard. Each cyclopropyl analog was examined over a dosage range of 1–25 ug (total dose).

The uterotropic assay was also used to evaluate the anti-estrogenic activity of the test compounds which did not produce an estrogenic response in the previous assay. The anti-estrogenic assay was conducted as described above for estrogenic activity except that each animal in the cyclopropyl analog treatment groups received a standard stimulating dose of estradiol (0.04 ug). The test compounds and estradiol were administered separately at different injection sites to minimize possible physical interaction or reduce absorption of either compound. Anti-estrogenic activity was measured as a decrease in estradiol-stimulated uterotropic response in groups which received both the test compound and estradiol as compared to a group which was treated with estradiol alone.

A line of best fit was plotted for each compound which produced an estrogenic or anti-estrogenic response. Regression analysis was used to calculate each line. The slope of the response to each analog was compared to the slope of the estradiol response to determine parallelism in this assay system. The relative uterotropic activity of each compound was expressed as a percentage of estradiol activity.

Histological Preparation and Examination

Mouse uterine tissue was fixed in 10% formaldehyde, embeded in paraffin, sectioned on a microtome and stained with hemotoxylin-eosin. Slides were examined with a compound light microscope and various measurements of uterine horn cross sections were made. These measurements, which were made on each cross section at several levels along the uterine horn, included: (1) total uterine horn diameter or thickness, at two different points (2) endometrial thickness at two different points as measured from the endometrial-myometrial border to maximum invagination of the endometrium into the lumen of the uterine horn. Photomicrographs of uterine horn cross sections and ephithelial linings were taken with a camera attached to a compound light microscope.

Anti-fertility Assay

Adult (8 week old) Swiss-Webster mice were used in the anti-fertility assay. The female mice were randomized into dosage groups containing 8 mice/group. The test compounds were dissolved in sesame oil and administered by subcutaneous injection in a total volume of 0.1 ml. The control group received an equal volume of sesame oil. The female mice were dosed daily for 23 consecutive days. Males of known fertility were caged with the females (1 male/4 females) from treatment days 8-20. During this period the females were checked for vaginal plugs and body weights were recorded weekly. The females were sacrificed on day 27 and the uterine horns examined for the number of fetuses and any gross malformation. In addition, the fetal weights were recorded.

Receptor Binding Assay

Uteri were removed from female Sprague-Dawley rats weighing approximately 250 g. The uteri were cleaned of connective tissue and homogenized in 5 vol. (w/v) ice-cold Tris buffer A containing 0.02 M Tris (hydroxymethyl) aminomethane hydrochloride, 0.0015 M disodium ethylenediamine tetraacetate, 0.25 M sucrose and the pH was adjusted to 7.4. The tissue was homogenized using a motor driven ground glass tissue homogenizer placed in an ice-water bath. The hemogenate was cetrifuged at $100,000 \times g$ for 1 hour at 4° C. using a swinging bucket rotor on an ultracentrifuge.

The supernatant (cytosol) was used immediately after preparation in the receptor binding assay. Incubations were conducted for 20 hours at 4° C. in a total volume of 0.5 ml of Tris buffer A containing 100-150 ul uterine cytosol, 0.025 uCi 2,4,6,7 (n)-[$^3$H]-17B-estradiol (327 mCi/mg) and various concentrations of the test compounds. Each test compound was assayed at 3 concentrations over a range of $10^{-4}$ to $10^{-6}$ molar for the cyclopropyl analogs and $10^{-7}$ to $10^{-9}$ molar for the estradiol standard. The test compounds were dissolved in ethanol and in all cases the final concentration of the ethanol was less than 2% of the incubation media. At the end of the incubation period the cytosolbound [$^3$H]-estradiol was separated from unbound [$^3$H]-estradiol by the addition of 0.5 ml of a Dextran-coated charcoal solution (Tris buffer A containing 0.05% Dextran-70 and 0.5% Norit A charcoal). The assay tubes were vortexed and centrifuged at $500 \times g$ for 15 min. The [$^3$H]-estradiol concentration of a 0.5 ml aliquot of the supernatant was determined by liquid scintillation spectrometry. Counting times were automatically adjusted to obtain a counting error of less than 1% using a liquid scintillation counter. The [$^3$H]-estradiol displacement for each test compound was determined by linear regression analysis and plotted graphically.

BIOLOGICAL RESULTS

The analogs set forth in Table I were tested to determine their estrogenic and anti-estrogenic activity using the uterotropic assay. The relative estrogenic activity of the analogs was determined to be that the estrogenic activity of analog VIII>analog IV>analog V. These analogs produced between 1.5% and 2.5% of the uterotropic response of estradiol on a molecular weight basis as reported in Table II hereinafter. Cyclopropyl analogs which displayed no estrogenic activity in the uterotropic assay were further tested for anti-estrogenic activity. As shown by the data of Table II, only analog II produced an anti-estrogenic response.

Since the uterotropic response is a nonspecific measure of estrogenic activity, the uteri were examined histologically to confirm the estrogenic nature of the uterotropic response. Estradiol and the cyclopropyl analogs (IV and VIII) produced a significant (P<0.001) increase in uterine diameter and endometrial thickness which represents a specific estrogenic response (Table III).

The cyclopropyl analogs were tested for receptor binding activity and compared to the estradiol standard. All of the analogs were capable of displacing [$^3$H]-estradiol from the estrogen receptor. However, analogs IV, VIII and V (in that order) displayed the greatest binding activity which ranged from 4% to 50% of the receptor binding activity produced by estradiol on a molecular weight basis (Table II).

The estrogen (analog VIII) and the anti-estrogen (analog II) were tested for anti-fertility activity using estradiol

TABLE II

Estrogenic, Anti-estrogenic and Receptor Binding Activity of the Cyclopropyl Analogs.

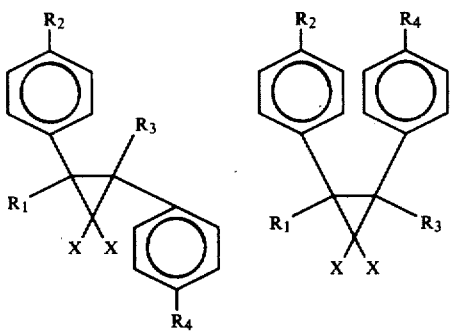

| Compound No. | Configuration | X | $R_1$ | $R_3$ | $R_2$ & $R_4$ | Relative Uterotropic Activity[a] | Antiestrogenic Activity[b] | Relative Receptor Binding Activity[c] |
|---|---|---|---|---|---|---|---|---|
| Estradiol | | | | | | 100 | — | 100 |
| Analog I | Trans | Cl | H | H | H | — | — | 0.02 |
| Analog II | Cis | Cl | H | H | H | — | 36 ug | 0.0086 |
| Analog III | Trans | H | $C_2H_5$ | $C_2H_5$ | $OCH_3$ | — | — | 0.4 |
| Analog IV | Trans | Cl | $C_2H_5$ | $C_2H_5$ | OH | 1.63 | — | 48.6 |
| Analog V | Trans | Cl | $C_2H_5$ | $C_2H_5$ | $OCOCH_3$ | 1.57 | — | 3.6 |
| Analog VI | Trans | Cl | H | H | $OCH_3$ | — | — | 0.0038 |
| Analog VII | Trans | Cl | $C_2H_5$ | $C_2H_5$ | $OCH_3$ | — | — | 0.049 |
| Analog VIII | Trans | H | $C_2H_5$ | $C_2H_5$ | OH | 2.55 | — | 9.1 |
| Analog IX | Cis | H | H | H | H | — | — | 0.0045 |
| Analog X | Trans | H | H | H | H | — | — | 0.0064 |

[a]Activity expressed as a percentage of estradiol activity.
[b]Dose of analog which would produce a 50% reduction in the uterotropic response to 0.04 ug estradiol.
[c]Concentration of estradiol that displaced 70% [$^3$H]-estradiol ÷ concentration of analog that displaced 70% [$^3$H]-estradiol × 100.

TABLE III

Histological Examination of Uterine Sections.

| Compound | Dose (ug) | Uterine Diameter (mm) Mean ± SD | Edometrial Thickness (mm) Mean ± SD |
|---|---|---|---|
| Control | — | 0.56 ± 0.15 | 0.16 ± 0.04 |
| Estradiol | 0.04 | 1.42 ± 0.24[a] | 0.49 ± 0.15[a] |
| Analog IV | 5.0 | 1.53 ± 0.19[a] | 0.48 ± 0.12[a] |
| Analog VIII | 5.0 | 1.30 ± 0.15[a] | 0.40 ± 0.07[a] |

[a]Significantly different from control P < 0.001.

TABLE IV

Antifertility Activity of Active Estrogenic and Antiestrogenic Cyclopropyl Analogs.

| Compound | Daily Dose (mg) | No. Pregnant/Group | No. Implants/Mouse Means ± SD | Fetal wt. (g)/ Group Mean ± SD |
|---|---|---|---|---|
| Control | — | 6/8 | 11.2 ± 3.25 | 7.5 ± 3.33 |
| Estradiol | 0.033 | 0/8 | 0 | — |
| Analog II | 16.7 | 6/8 | 10.3 ± 1.86 | 7.5 ± 5.07 |
| Analog VIII | 4.2 | 0/8 | 0 | — | as a standard anti-fertility agent. Both estradiol and analog VIII exhibited good anti-fertility activity (Table IV). The anti-estrogen (analog II) produced no anti-fertility effect; however, one female in this treatment group had pups which were markedly underdeveloped with a total fetal weight of 0.9 g/10 pups as compared to the group mean of 7.5 g/110.3 pups.

Each of the cyclopropyl analogs set forth in this Example were found to bind, in a specific manner, to the estrogen receptor. Thus, it is apparent that the estrogenic cyclopropyl analogs of the present invention have potential as effective anti-fertility and general estrogenic agents.

EXAMPLE II

A series of cyclopropyl analogs were prepared using the procedures A, B, and C set forth in Example I, and the cyclopropyl analogs so prepared were subjected to a series of experiments to determine the estrogen receptor binding activity of each of the analogs tabulated in Table V. The estrogen receptor binding activities of the analogs of Table V are reported in Table VI.

TABLE V

| | CYCLOPROPYL ANALOGS |
|---|---|
| Analog No. | Chemical Name |
| XI | 1,1-dichloro-trans-2-methyl-2,3-(4,4'-dimethoxydiphenyl)cyclopropane |
| XII | 1,1-dichloro-trans-2,3-dimethyl-2,3-(4,4'-dimethoxydiphenyl)cyclopropane |
| XIII | 1,1-dichloro-trans-2-methyl-2,3-diphenylcyclopropane |
| XIV | 1,1-dichloro-trans-2,3-dimethyl-2,3-diphenylcyclopropane |
| XV | 1,1-dichloro-cis-2-methyl-2,3-diphenylcyclopropane |
| XVI | 1,1-dichloro-cis-2,3-dimethyl-2,3-diphenylcyclopropane |
| XVII | 1-methyl-trans-1,2-(4,4'-dimethoxydiphenyl)cyclopropane |
| XVIII | trans-1,2-dimethyl-1,2-(4,4'-dimethoxydiphenyl)cyclopropane |
| XIX | trans-1-methyl-1,2-diphenylcyclopropane |

TABLE V-continued

| | CYCLOPROPYL ANALOGS |
|---|---|
| Analog No. | Chemical Name |
| XX | trans-1,2-Dimethyl-1,2-diphenylcyclopropane |
| XXI | cis-1-methyl-1,2-diphenylcyclopropane |

BIOLOGICAL RESULTS

Each analog as set forth in Table V was tested initially in the uterotropic assays for estrogenic and anti-estrogenic activity as described in Example I. It was determined that none of the analogs listed in Table V displayed estrogenic or anti-estrogenic activity in the assay system employed.

The cyclopropyl analogs listed in Table V, were further tested for receptor binding activity as described in Example I. The data tabulated in Table VI indicates that all of the analogs listed in Table V were capable of specific binding to the estrogen receptor.

Each of the cyclopropyl Analogs set forth in this Example were found to bind, in a specific manner, to the estrogen receptor.

TABLE VI

Receptor Binding Activity of the Cyclopropyl Analogs.

| Compound No. | Isomer Configuration | X | $R_1$ | $R_3$ | $R_2$ & $R_4$ | Relative Binding Activity$^a$ (% Estradiol Response) |
|---|---|---|---|---|---|---|
| Estradiol | | | | | | 100 |
| XI | trans | Cl | $CH_3$ | H | $O-CH_3$ | $8.3 \times 10^{-5}$ |
| XII | trans | Cl | $CH_3$ | $CH_3$ | $O-CH_3$ | $5.9 \times 10^{-4}$ |
| XIII | trans | Cl | $CH_3$ | H | H | $5.4 \times 10^{-4}$ |
| XIV | trans | Cl | $CH_3$ | $CH_3$ | H | $5.1 \times 10^{-4}$ |
| XV | cis | Cl | $CH_3$ | H | H | $6.3 \times 10^{-4}$ |
| XVI | cis | Cl | $CH_3$ | $CH_3$ | H | $5.5 \times 10^{-4}$ |
| XVII | trans | H | $CH_3$ | H | $O-CH_3$ | $7.3 \times 10^{-4}$ |
| XVIII | trans | H | $CH_3$ | $CH_3$ | $O-CH_3$ | $2.2 \times 10^{-3}$ |
| XIX | trans | H | $CH_3$ | H | H | $1.5 \times 10^{-4}$ |
| XX | trans | H | $CH_3$ | $CH_3$ | H | $1.1 \times 10^{-4}$ |
| XXI | cis | H | $CH_3$ | H | H | $8.0 \times 10^{-4}$ |

$^a$ $\dfrac{\text{Concentration of estradiol that displaced 50\% [}^3\text{H]-estradiol}}{\text{Concentration of analog that displaced 50\% [}^3\text{H]-estradiol}} \times 100$ Thus, it is apparent that the cyclopropyl analogs of the present inention have potential as effective anti-fertility agents to prevent ovulation, implantation and pregnancy. However, analog II exhibited substantially greater anti-estrogenic activity and less uterotropic activity than the other analogs of Table I and thus would not be suitable as an anti-fertility agent. Thus analog II is specifically excluded from the compounds represented by Structure I, which would be suitable as anti-fertility agents.

It is clear that the present invention is well adapted to carry out the objects and attain the ends and advantages mentioned, as well as those inherent therein. While a presently preferred embodiment has been described for purposes of this disclosure, numerous changes may be made which will readily suggest themselves to those skilled in the art and which are encompassed within the spirit of the invention disclosed and as defined in the appended claims.

What is claimed is:

1. A method of treating a normal or pathological condition responsive to estrogenic activity in a female subject in need of such therapy comprising administering to the subject an estrogenically effective, non-toxic dosage of an agent having the generic structure:

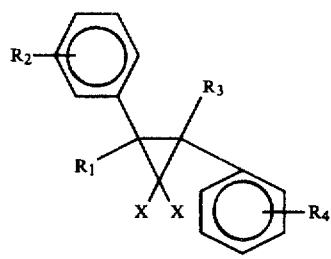

wherein:
X is a halogen or hydrogen atom;
$R_1$ is a hydrogen atom, an alkyl group, containing from 1 to about 3 carbon atoms, a monocyclic group, or an alkoxy substituted monocyclic group in which the alkyl substituent contains from 1 to about 3 carbon atoms;
$R_2$ is a hydroxyl group;
$R_3$ is a hydrogen atom or an alkyl group containing from 1 to about 3 carbon atoms; and
$R_4$ is a hydrogen atom, a hydroxyl group, or an alkoxy group in which the alkyl substituent contains from 1 to about 3 carbon atoms.

2. The method of claim 1 wherein $R_4$ is a hydroxyl group.

3. The method of claim 1 wherein $R_1$ and $R_3$ are each an alkyl group containing from 1 to about 3 carbon atoms.

4. The method of claim 3 wherein $R_4$ is a hydroxyl group.

5. The method of claim 1 wherein $R_1$ and $R_3$ are each ethyl groups.

6. The method of claim 5 wherein $R_4$ is a hydroxyl group.

7. The method of claim 6 wherein X is a chlorine atom.

8. The method of claim 6 wherein X is a hydrogen atom.

9. A method of treating a normal or pathological condition responsive to estrogenic activity in a female subject in need of such therapy comprising administering to the subject an estrogenically effective, non-toxic dosage of an agent having the generic structure:

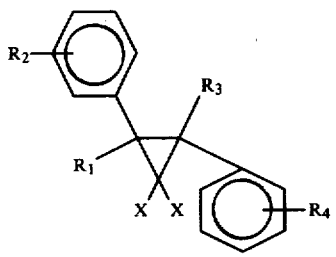

wherein:

X is a halogen or hydrogen atom;

$R_1$ is a hydrogen atom, an alkyl group, containing from 1 to about 3 carbon atoms, a monocyclic group, a hydroxy substituted monocyclic group, or an alkoxy substituted monocyclic group in which the alkyl substitutent contains from 1 to about 3 carbon atoms;

$R_2$ is a hydrogen atom, a hydroxyl group, an alkoxy group in which the alkyl substituent contains from 1 to about 3 carbon atoms, a beta-dialkylaminoethoxy group wherein the alkyl substituent contains from 1 to about 3 carbon atoms, a beta-monoaminoheterocycloethoxy group, or pharmaceutically acceptable salts thereof;

$R_3$ is a hydrogen atom or an alkyl group containing from 1 to about 3 carbon atoms; and $R_4$ is a hydrogen atom, a hydroxyl group, or an alkoxy group in which the alkyl substituent contains from 1 to about 3 carbon atoms.

10. The method of claim 9 wherein the estrogenic cyclopropyl analog is administered to the subject in an amount of about 0.5 milligram to about 2 milligrams per kilogram of body weight of the subject.

11. The method of claim 9 wherein X is a chlorine, fluorine or bromine atom, and $R_1$, $R_2$, $R_3$, and $R_4$ are hydrogen atoms.

12. The method of claim 9 wherein X is a chlorine atom.

13. The method of 12 wherein:

X is a chlorine, fluorine, or bromine atom;

$R_1$ is a phenyl group, p-hydroxyphenyl group or p-methoxyphenyl group;

$R_2$ is a beta-dimethylaminoethoxy group, a beta-diethylaminoethoxy group, a beta-pyrrolidinoethoxy group, or pharmaceutically acceptable salts thereof;

$R_3$ is an ethyl group; and $R_4$ is a hydrogen atom, a hydroxyl group, or a methoxy group.

14. The method of claim 12 wherein:

$R_2$ is a hydroxyl group or an acetate group; and $R_4$ is a hydroxyl group or an acetate group.

15. The method of claim 14 wherein the estrogenic cyclopropyl analog is administered to the subject in an amount of about 0.5 milligrams to about 2 milligrams per kilogram of body weight of the subject.

16. The method of claim 14 wherein $R_1$ and $R_3$ are alkyl groups containing from about 1 to about 3 carbon atoms.

17. The method of claim 16 wherein $R_1$ and $R_3$ are ethyl moieties.

18. The method of claim 17 wherein each X is a hydrogen atom.

19. The method of claim 17 wherein each X is a chlorine atom.

* * * * *